(12) United States Patent
Liu

(10) Patent No.: US 11,241,571 B2
(45) Date of Patent: Feb. 8, 2022

(54) IMPLANTABLE VENTRICULAR ASSIST DEVICE

(71) Applicant: Marvin Liu, Diamond Bar, CA (US)

(72) Inventor: Marvin Liu, Diamond Bar, CA (US)

(*) Notice: Subject to any disclaimer, the term of this patent is extended or adjusted under 35 U.S.C. 154(b) by 6 days.

(21) Appl. No.: 16/581,697

(22) Filed: Sep. 24, 2019

(65) Prior Publication Data

US 2021/0085849 A1    Mar. 25, 2021

(51) Int. Cl.
| | |
|---|---|
| *A61M 60/148* | (2021.01) |
| *A61F 2/90* | (2013.01) |
| *A61M 60/40* | (2021.01) |
| *A61M 60/274* | (2021.01) |
| *A61M 60/869* | (2021.01) |

(Continued)

(52) U.S. Cl.
CPC .......... *A61M 60/148* (2021.01); *A61F 2/90* (2013.01); *A61M 60/17* (2021.01); *A61M 60/187* (2021.01); *A61M 60/274* (2021.01); *A61M 60/40* (2021.01); *A61M 60/497* (2021.01); *A61M 60/857* (2021.01); *A61M 60/869* (2021.01); *A61F 2210/0014* (2013.01); *A61F 2250/0067* (2013.01); *A61M 2205/0216* (2013.01); *A61M 2205/0266* (2013.01); *A61M 2205/07* (2013.01); *A61M 2205/3317* (2013.01);

(Continued)

(58) Field of Classification Search
CPC .......... A61M 60/148; A61M 60/857; A61M 60/869; A61M 60/274; A61M 60/40; A61M 2210/125; A61M 2205/0216; A61M 2205/3317; A61M 2230/04; A61M 2205/07; A61M 2205/0266; A61F 2/90; A61F 2210/0014; A61F 2250/0067
See application file for complete search history.

(56) References Cited

U.S. PATENT DOCUMENTS 7,530,998 B1    5/2009  Starkey
9,623,163 B1 *  4/2017  Fischi .................. A61M 60/40
(Continued)

FOREIGN PATENT DOCUMENTS

CN    108125728 A    6/2016
CN    108888813 A    11/2018
(Continued)

*Primary Examiner* — Jerrah Edwards
*Assistant Examiner* — Jared Klar Rovira

(57) ABSTRACT

An implantable ventricular assist device comprises an intraventricular stent used for the creation of an artificial chamber inside the ventricle, a balloon-like structure used to drive the change of the artificial chamber between a contractile configuration and a diastolic configuration, a power system used for driving the change of the balloon-like structure between the contractile configuration and the diastolic configuration. There is also a power system and a mechanical design to operate the system working, wherein in the contractile configuration, the balloon-like structure expands and occupies the space of the artificial chamber and drives the blood inside the artificial chamber flow outside the artificial chamber, wherein in the diastolic configuration, the balloon-like structure shrinks and releases the space inside the artificial chamber, and the blood outside the artificial chamber flows back into the artificial chamber. It is easy to reach the goal of cardiac function.

14 Claims, 15 Drawing Sheets

(51) Int. Cl.
    *A61M 60/497*     (2021.01)
    *A61M 60/17*     (2021.01)
    *A61M 60/187*     (2021.01)
    *A61M 60/295*     (2021.01)
    *A61M 60/857*     (2021.01)

(52) U.S. Cl.
    CPC ... *A61M 2210/125* (2013.01); *A61M 2230/04* (2013.01)

(56) References Cited

U.S. PATENT DOCUMENTS

| | | | |
|---|---|---|---|
| 2004/0243170 A1* | 12/2004 | Suresh | A61F 2/2487 606/198 |
| 2013/0184515 A1* | 7/2013 | Ovil | A61M 60/50 600/17 |
| 2013/0261545 A1* | 10/2013 | Osypka | A45C 5/03 604/103.02 |
| 2015/0290370 A1* | 10/2015 | Crunkleton | A61B 17/11 600/16 |
| 2017/0095333 A1 | 4/2017 | Rowe | |
| 2017/0290966 A1* | 10/2017 | Botterbusch | A61M 60/268 |
| 2018/0256795 A1 | 9/2018 | Schade et al. | |

FOREIGN PATENT DOCUMENTS

| | | | |
|---|---|---|---|
| JP | 2010220833 A | 10/2010 | |
| WO | 2016041220 A1 | 3/2016 | |
| WO | 2016110735 A1 | 7/2016 | |
| WO | 2018177344 A1 | 10/2018 | |

\* cited by examiner

IMPLANTABLE VENTRICULAR ASSIST DEVICE

FIELD OF THE INVENTION

The present invention relates to ventricular assist device and in particular to implantable ventricular assist device.

DESCRIPTION OF THE RELATED ART

Cardiovascular disease is the leading cause of death in the world, which includes coronary artery diseases such as angina and myocardial infarction, the others such as heart failure, hypertensive heart disease, rheumatic heart disease, cardiomyopathy and heart arrhythmia. Heart failure is when the heart is unable to pump sufficiently to maintain blood flow to meet the body's needs, and has been one of the most common causes of death in cardiovascular disease, also known as congestive heart failure (CHF). It affected about 40 million people globally. Overall around 2% of adults have heart failure and in those over the age of 65, this increase to 6-10%. The risk of death is about 35% the first year after diagnosis and about 10% the year following, and similar to some cancers. Treatment depends on the severity and the underline cause of the disease. In people with chronic stable mild heart failure, treatment commonly consists of lifestyle modifications and medications. In those with severe heart failure, ventricular assist device or heart transplant has been the choice for most of the patients.

A ventricular assist device is a mechanical pump that help pump blood from ventricles to the rest of body for the partially or completely replace the failed cardiac function, which includes pulsatile pumps as an inflatable cuff around the aorta, that mimic the natural pulsing action of the heart, and continuous flow pumps which are driven by an axial flow rotor, a magnetically suspended axial flow rotor, a hydrodynamically suspended centrifugal rotor, a magnetically suspended centrifugal rotor, magnetically levitated centrifugal pump. Some are for short-term use, some are for long-term use. However, all of them are the mechanical blood pumping device only and do not effectively integrate the anatomical and physiological properties of the heart. Magnetically levitated centrifugal pump as the most sufficient ventricular assist device so far, has many unsolved problem in clinical use, such as cardiac rupture, hemorrhage and infection, lifetime anticoagulation, non-pulsatile perfusion and high cost. Therefor it is important to find a new way to raise the ability to support cardiac function for the patients with heart failure.

SUMMARY OF THE INVENTION

It is the object of the present invention to provide an implantable ventricular assist device with no rotor or centrifuge to pump blood out of ventricles.

The present invention provides the implantable ventricular assist device comprising:

an intraventricular stent used for the creation of an artificial chamber inside the ventricle by a three-dimensional mesh-like hollow supporting structure;

a balloon-like structure is disposed inside the intraventricular stent to drive the change of the artificial chamber between a contractile configuration and a diastolic configuration, wherein in the contractile configuration, the balloon-like structure expands and occupies the space of the artificial chamber and drives the blood inside the artificial chamber flow to outside the artificial chamber through the mesh-like structure of the intraventricular stent; wherein in the diastolic configuration, the balloon-like structure shrinks and releases the space inside the artificial chamber, and the blood outside the artificial chamber flows back into the artificial chamber through the mesh-like structure of the intraventricular stent;

a power system for driving the change of the balloon-like structure between the contractile configuration and the diastolic configuration.

The implantable ventricular assist device includes a cage-like intraventricular stent, the balloon-like structure, a tube and the power system, wherein:

the cage-like intraventricular stent is a closed three-dimensional hollow mesh-like structure, and forms a closed cage-like artificial chamber by itself;

the balloon-like structure disposed inside the cage-like intraventricular stent comprises a connector and a retractable three-dimensional balloon-like structure, and the connector is connected with the tube;

the tube is used for the connection between the power system and the balloon-like structure; wherein in the contractile configuration, the power system raises the pressure in the balloon-like structure, so the balloon-like structure expands, and the blood inside the artificial chamber is driven outside the artificial chamber into the ventricle, and then the blood in the ventricle is driven to flow into the artery through the artery valve; wherein in the diastolic configuration the power system decompresses the balloon-like structure, shrinks the balloon-like structure, releases the space inside the artificial chamber, and sucks the blood in the ventricle flow into the artificial chamber, and then sucks the blood from the atrium flow into the ventricle through the atrioventricular valve.

The implantable ventricular assist device includes a fence-surround intraventricular stent, the balloon-like structure, a tube and the power system, wherein:

the fence-surround intraventricular stent is a three-dimensional hollow mesh-like structure with open end, and forms a closed artificial chamber by a fence-surrounded and ventricular wall combined;

the balloon-like structure is disposed inside the fence-surround intraventricular stent comprising a connector and a retractable three-dimensional balloon-like structure, and the connector is connected with the tube;

the tube is used for the connection between the power system and the balloon-like structure; wherein in the contractile configuration, the power system raise the pressure in the balloon-like structure, so the balloon-like structure expands, and the blood inside the artificial chamber is driven outside the artificial chamber into the ventricle, and then the blood in the ventricle is driven to flow into the artery through the artery valve; wherein in the diastolic configuration, the power system decompresses the balloon-like structure, shrinks the balloon-like structure, releases the space inside the artificial chamber, and the blood in the ventricle flows back into the artificial chamber, and then the blood is sucked from the atrium and flow into the ventricle through the atrioventricular valve.

The power system comprises a double chamber extrusion driving system, which is mediated by a driving medium comprising at least one of the mediums of liquid and gas.

The power system comprises a magnetic squeeze drive structure which is used for driving the changes of the balloon-like structure between the contractile configuration and diastolic configuration, and comprises a driving pad, a driving chamber, a driving medium, a driving tube and a driving holder, with at least one of the following characteristics:

1) the driving chamber provided on the driving holder is a soft structure with a resilient outer wall and adjacent to a first driving pad and a second driving pad; the first driving pad is attached on the one side of the resilient outer wall of the driving chamber and further fixed on the one side of the driving holder, and the second driving pad is attached on the opposite side of the resilient outer wall of the driving chamber and free from the driving holder, the driving chamber is filled with the driving medium, and the first driving pad may have a magnetic field generator and the second driving pad may have a magnetic material which is attracted to the magnetic field generator when the magnetic field generator generates a magnetic field, thereby when the first driving pad generates a magnetic field and the second driving pad is attracted to the first driving pad and moves toward the first driving pad, so the driving chamber is compressed and it drives the driving medium inside the driving chamber into the balloon-like structure through the driving tube and expands the balloon-like structure to the contractile configuration, and further when the first driving pad stops to generate a magnetic field and the second driving pad is not attracted to the first driving pad and released from the first driving pad, the driving chamber is decompressed and restored by actuating the resilient outer wall of the driving chamber along with the second driving pad, and then sucks the driving medium in the balloon-like structure flow back into the driving chamber and shrinks the balloon-like structure to the diastolic configuration.

2) the driving chamber provided on a driving holder is a soft structure and adjacent to a third driving pad, a fourth driving pad, a fifth driving pad and the driving holder, the third driving pad is disposed on the one side of the outer wall of the driving chamber and further fixed on the one side of the driving holder, the fourth driving pad is disposed on the outer wall of the driving chamber at the opposite side of the third driving pad and free from the driving holder, and the fifth driving pad is disposed and fixed on the driving holder at the opposite side of the third driving pad, and the third driving pad may have a magnetic field generator and the fourth driving pad may have a magnetic material which is attracted to the magnetic field generator when the magnetic field generator generates a magnetic field, the driving chamber is filled with the driving medium, thereby when the third driving pad generates a magnetic field and the fourth driving pad is attracted to the third driving pad and moves toward the third driving pad, the driving chamber is compressed and it drives the driving medium inside the driving chamber into the balloon-like structure through the driving tube and expands the balloon-like structure to the contractile configuration, and further when the third driving pad stops to generate a magnetic field and the fourth driving pad is not attracted to the third driving pad anymore and released from it, and the fifth driving pad generates a magnetic field, the fourth driving pad is attracted to the fifth driving pad and moves toward the fifth driving pad, the driving chamber is decompressed and restored by the recovery of the outer wall of the driving chamber along with the fourth driving pad, and sucks the driving medium in the balloon-like structure flow back to the driving chamber and shrinks the balloon-like structure to the diastolic configuration.

3) the driving chamber provided on a driving holder is a soft structure and adjacent to a sixth driving pad, a seventh driving pad and the driving holder, the sixth driving pad is disposed on one side of the outer wall of the driving chamber and further fixed on the one side of the driving holder, and the seventh driving pad is disposed on the opposite side of the resilient outer wall of the driving chamber and free from the driving holder, the driving chamber is filled with the driving medium, the sixth driving pad and the seventh driving pad may have a polar magnetic field generator, thereby the sixth driving pad and the seventh driving pad generate a magnetic field with the opposite polarity toward each other, so the seventh driving pad is attracted to the sixth driving pad, the seventh driving pad moves toward the sixth driving pad, and the driving chamber is compressed and then it drives the driving medium inside the driving chamber into the balloon-like structure through the driving tube and expands the balloon-like structure to the contractile configuration, and further when either the sixth driving pad or the seventh driving pad changes the polarity of magnetic field to opposite direction, the seventh driving pad is not attracted to the sixth driving pad any more, instead their mutually repel moves the seventh driving pad away from the sixth driving pad, so the driving chamber is decompressed and recovered by the actuating of pulling back toward the outer wall of the driving chamber along with the seventh driving pad, and sucks the driving medium inside the balloon-like structure flow back to the driving chamber and shrinks the balloon-like structure to the diastolic configuration;

4) the magnetic field generator is an electromagnet;

5) the magnetic field generator is a permanent magnet;

6) the polarity of the electromagnet is controlled by changing the polarity of the electric power supply;

7) the action site of the driving magnetic field of permanent magnet is controlled by the translocation of permanent magnet;

8) the magnetic field generator is provided on a driving holder, and the action site of the magnetic field is adjustable by the translocation of the magnetic field generator on the driving holder.

The activity of the balloon-like structure is controlled by ECG signal, the driving system includes an electrical energy supply electrically connected to the magnetic field generator, a controller which controls the electric energy supply to turn either on or off the magnetic field generation, and an ECG signal generator which connect to the controller generates a signal when there is ventricular systole and ventricular diastole, wherein the controller controls the balloon-like structure expanded when the ECG signal generator signals the controller that there is ventricular systole and wherein the controller controls the balloon-like structure shrinked when the ECG signal generator signals the controller that there is ventricular diastole.

The activity of the balloon-like structure is self-controlled, the driving system includes an electrical energy supply electrically connected to the magnetic field generator, a controller which controls the electric energy supply to turn either on or off the magnetic field generation and controls the change of contractile configuration and diastolic configuration; and an driving program including a contractile rhythm, diastolic rhythm, contractile duration and diastolic duration is set up in the controller; wherein the controller controls the balloon-like structure expanded when the controller generates a signal that there is contractile rhythm and wherein the controller controls the balloon-like structure to shrink when the controller generates a signal that there is diastolic rhythm.

The intraventricular stent may include a radially compressible and expandable anchor member which can be deployed inside the inner surface of ventricular wall and the inner surface just below the atriovantricular valve and further keep a right shape of ventricle.

The power system may further include an internal driving pad inside the body and an external driving pad outside the body; the internal driving pad may be a material with permanent magnetic field and the external driving pad may have a magnetic material which is attracted to the magnetic field generator when the magnetic field generator generates or has a magnetic field, and the internal driving pad attaches on the one side of the outer wall of the driving chamber inside the body and the external driving pad is free from the outer wall of the driving chamber just at the opposite site of the internal driving pad cross the chest wall, wherein it may have the magnetic field on and off at the action site and pumps the driving medium circulate inside the portion inside the body, and drives the change of the balloon-like structure between the contractile configuration and diastolic configuration.

The internal driving pad may be a material with permanent magnetic field and the external driving pad may be a magnetic material with permanent magnetic field as well, and the external driving pad is free from the outer wall of the driving chamber just at the opposite site of the internal driving pad cross the chest wall, and may move on and move away from the action site and provide the squeezing pressure to the driving chamber to pump the driving medium circulating inside the portion inside the body, and drives the change of the balloon-like structure between the contractile configuration and diastolic configuration.

The implantable ventricular assist device is a communication setting through a driving medium between outside the body and inside the body, which comprises the intraventricular stent, the balloon-like structure, a driving pad, a driving chamber, a power supply, the driving medium and a driving tube; the driving chamber is filled with the driving medium, wherein the portion inside the body includes the intraventricular stent, the balloon-like structure, and the internal part of the driving tube, wherein the portion outside the body includes the driving pad, the power supply and the driving chamber and the external part of the driving tube, and further the inside and outside portions of the implantable ventricular assist device are communicated by the driving tube across the chest wall, the driving medium circulates between the inside and outside portions of the implantable ventricular assist device, and it drives the change of the balloon-like structure between the contractile configuration and diastolic configuration.

The implantable ventricular assist device is an separated setting with no direct contact and no driving medium directly mediated communication between the portion outside the body and the portion inside the body, which comprises the intraventricular stent, the balloon-like structure, a driving pad, a driving chamber, a power supply, a driving medium and a driving tube, and further the driving pad is a magnetic squeezing structure, which includes an internal driving pad inside the body and an external driving pad outside the body, wherein the internal driving pad attaches on the one side of the outer wall of the driving chamber inside the body and the external driving pad is free from the outer wall of the driving chamber just at the opposite site of the internal driving pad cross the chest wall, and these two pads provide the squeezing pressure to the driving chamber to drive the driving medium flow outside the driving chamber, and wherein the portion inside the body includes the intraventricular stent, the balloon-like structure, the driving chamber, the driving medium, the driving tube and the internal driving pad, wherein the portion outside the body includes the power supply, the external driving pad, further the internal driving pad may have a magnetic material which is attracted to the magnetic field generator when the magnetic field generator generates or can generate or has a magnetic field, and the external driving pad is a material which generates or can generate or has magnetic field, and the driving medium circulates within the inside portion of the implantable ventricular assist device in the body, and drives the change of the balloon-like structure between the contractile configuration and diastolic configuration.

The material for making the intraventricular stent has characteristics as flexible supporting materials with certain elasticity, memory metal and anti-thrombosis.

The material for making the balloon-like structure has the characteristics as soft materials with strong endurance, elasticity and anti-thrombosis.

The intraventricular stent is an external compression structure and made by memory metal or other flexible stent materials and integrated and compacted with the balloon-like structure before implantation, and after being implanted in the ventricle, the intraventricular stent extends and forms a three-dimensional hollow mesh-like supporting structure and apply a longitudinal and horizontal force against the inner surface of the ventricle to establish the artificial chamber.

The implantable ventricular assist device comprises an implantable compacted pack that can be delivered to the ventricle via the patient's vasculature in a minimally-invasive procedure and when it is deployed inside the ventricle, the implantable compacted pack is extended and adapted to apply a longitudinal force and horizontal force against the inner surface of the ventricle to establish the artificial chamber.

An application of the implantable ventricular assist device in the development of ventricular assist devices.

The present disclosure has following advantages due to the above technical solutions:

This invention utilizes the intraventricular stent as the shape supporter for the inner cavity of the ventricle and forms a hollow ventricular stent for support, and this maintains effective diastolic expansion of the ventricle. Furthermore, the balloon-like structure used in this invention is disposed within the intraventricular stent, and communicates with the driving system through the driving tube to fulfill the expansion and shrink process and effectively balances the change of the ventricle between systolic configuration and diastolic configuration. This process is very similar to how the heart naturally functions and it pumps the blood in the circulatory system in a pulsatile manner and has the atrium and ventricle working under normal physiological condition. Unlike the rotor motivation of the current ventricular assist device, this invention uses a double chamber extrusion driving system and drives the driving medium inside the chamber as liquid or gas flow between the two chambers through the driving tube, and keep the balloon-like structure expanded and shrinked to pump and suck the blood circulate in the heart, and it does not need any mechanical motor drive to keep blood flow.

The driving system used in this invention is a magnetic extrusion driving system. It uses a squeeze force instead of motor power. It is not only able to drive the blood flow inside the body effectively with the significantly reduction of energy consumption, but also it has been very easy to control from outside of the body and improve driving efficiency. Moreover, this driving system makes it possible for the external driving part outside the body with power supply to be separated with the internal driving part inside the body by the chest wall through the noninvasive setup, which makes it very easy to be controlled and further prevents infection and hemorrhage.

DETAILED DESCRIPTION OF EMBODIMENTS

This invention will be described in detail below with reference to the accompanying drawings and embodiments, but these embodiments are not intended to limit the invention.

Figure 1:
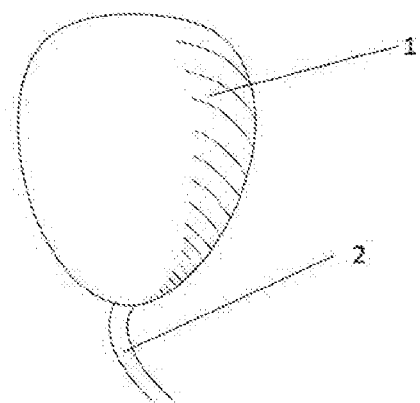
FIG. 1 is a schematic diagram of a balloon-like structure in expansion.
Figure 2:
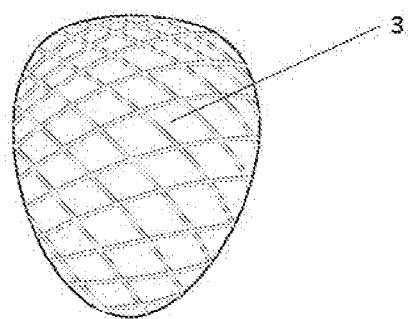
FIG. 2 is a schematic diagram of an intraventricular stent.
Figure 3:
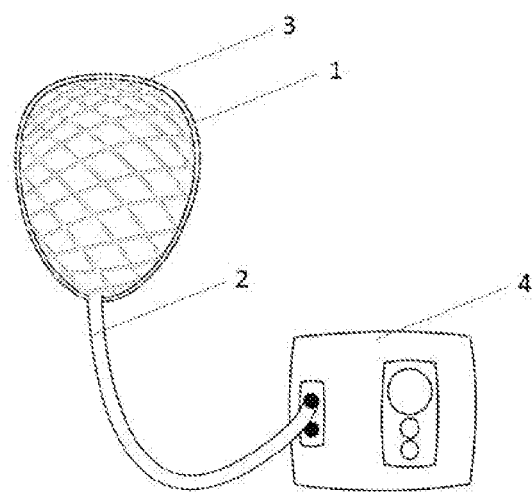
FIG. 3 is a schematic diagram of the balloon-like structure driven by the filling in and sucking off with the driving medium as liquid or gas.
Figure 4:
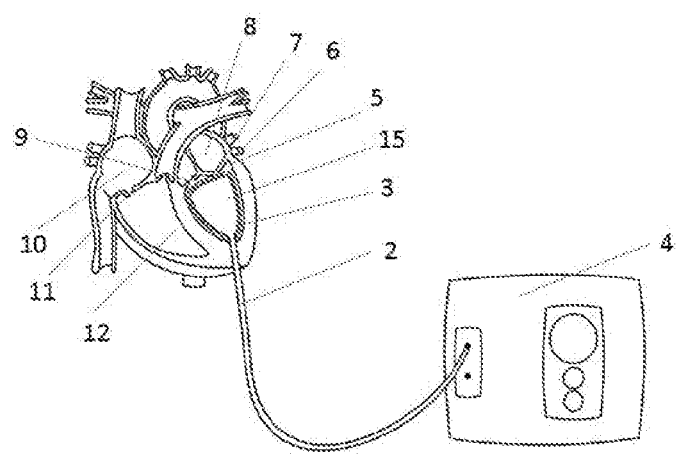
FIG. 4 is a schematic diagram of the balloon-like structure inside the cage-like intraventriclular stent driven by the filling in the driving medium as liquid or gas in left ventricle.
Figure 5:
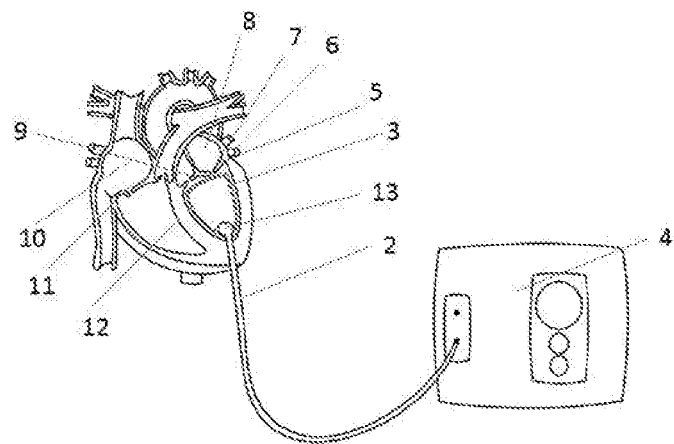
FIG. 5 is a schematic diagram of the balloon-like structure inside the cage-like intraventriclular stent driven by the sucking off the driving medium as liquid or gas in left ventricle.
Figure 6:
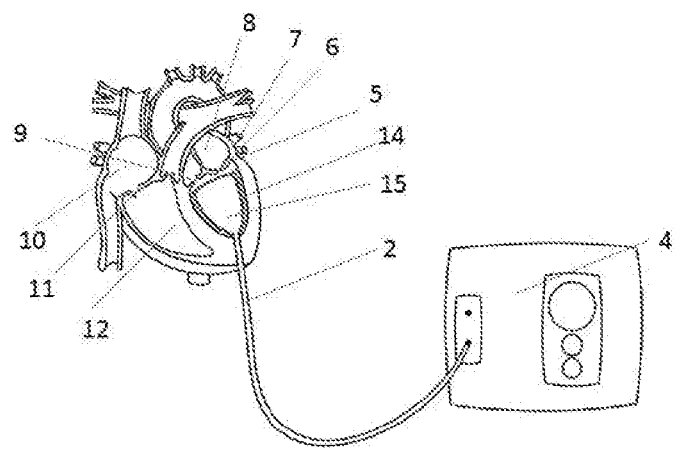
FIG. 6 is a schematic diagram of the balloon-like structure inside the fence-surround intraventriclular stent driven by the filling in the driving medium as liquid or gas in left ventricle.
Figure 7:
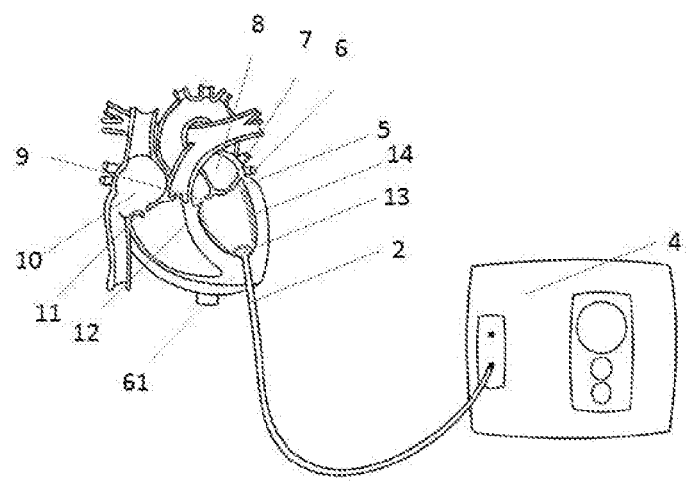
FIG. 7 is a schematic diagram of the balloon-like structure inside the fence-surround intraventriclular stent driven by the sucking off the driving medium as liquid or gas in left ventricle.

As shown in FIGS. 1-7, the structure of the invention for implantable ventricular assist device includes an intraventricular stent 3 for providing an artificial chamber with a three-dimensional mesh-like hollow supporting structure in the ventricle 5; a balloon-like structure 1 provided inside the intraventricular stent 3 for making a change of the artificial chamber between a contractile configuration and a diastolic configuration; and a power system 4 for driving the balloon-like structure 1 to convert between a contractile configuration and a diastolic configuration, where in the case that the balloon-like structure 1 expands to occupy a space in the artificial chamber as showed the occupied space surrounded by the intraventricular stent 3 in the left ventricle 5 in FIG. 4 and FIG. 6, having the three-dimensional mesh-like hollow supporting structure formed by the intraventricular stent 3, the balloon-like structure 1 is in the contractile configuration; while in the case that the balloon-like structure 1 shrinks to release the occupied space in the artificial chamber to make the artificial chamber have a hollow three-dimensional support structure as showed the released space surrounded by the intraventricular stent 3 in the left ventricle 5 in FIG. 5 and FIG. 7, the balloon-like structure 1 is in the diastolic configuration. There also have other components of the heart in these Figs. as right ventricle 12, tricuspid valve 11, right atrium 10, aortic valve 9, left ventricle 8, mitral valve 7, pulmonary vein 6, a driving tube 2.

As shown in FIGS. 3, 4, 5, the invention includes a cage-like intraventricular stent 3 with closed end for providing the artificial chamber with the three-dimensional mesh-like hollow supporting structure in the ventricle 5, the balloon-like structure 1 provided inside the cage-like intraventricular stent 3 with closed end for making a conversion of the artificial chamber between a contractile configuration and a diastolic configuration; and the power system 4 for driving the balloon-like structure 1 to conversion between a contractile configuration and a diastolic configuration, where in the case that the balloon-like structure 1 expands (the expansion state 15) to occupy a space in the artificial chamber having the three-dimensional mesh-like hollow supporting structure formed by the cage-like intraventricular stent 3 with closed end, the balloon-like structure 1 is in a contractile configuration with closed end as showed in FIG. 4; while in the case that the balloon-like structure 1 shrinks (the shrink state 13) to release the occupied space in the artificial chamber to make the artificial chamber have a hollow three-dimensional support structure, the balloon-like structure 1 is in a diastolic configuration with closed end as showed in FIG. 5.

As shown in FIGS. 3, 6, 7, the invention includes a fence-surround intraventricular stent 14 for providing the artificial chamber with the three-dimensional mesh-like hollow supporting structure in the ventricle 5 combined with a ventricular wall 61; the balloon-like structure 1 provided inside the fence-surround intraventricular stent 14 for making a conversion of the artificial chamber between a contractile configuration and a diastolic configuration; and the power system 4 for driving the balloon-like structure 1 to convert between a contractile configuration and a diastolic configuration, where in the case that the balloon-like structure 1 expands (the expansion state 15) to occupy a space in the artificial chamber having the three-dimensional mesh-like hollow supporting structure formed by the fence-surround intraventricular stent 14, the balloon-like structure 1 is in an contractile configuration with open end as showed in FIG. 6; while in the case that the balloon-like structure 1 shrinks (the shrink state 13) to release the occupied space in the artificial chamber to make the artificial chamber have a hollow three-dimensional support structure, the balloon-like structure 1 is in an diastolic configuration with open end as showed in FIG. 7.

Figure 8:
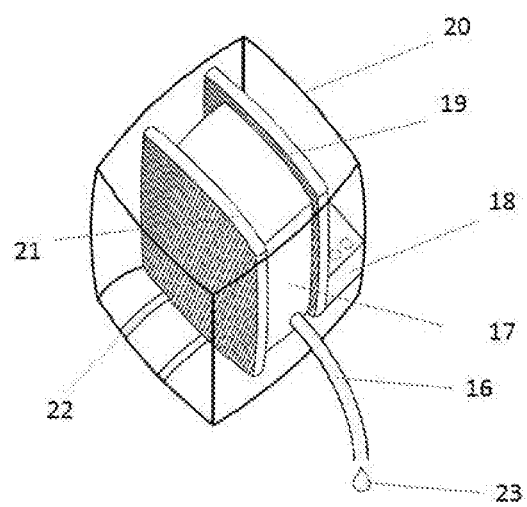
FIG. 8 is a schematic diagram of a magnetic squeeze drive structure of a single magnetic generator.
Figure 13:
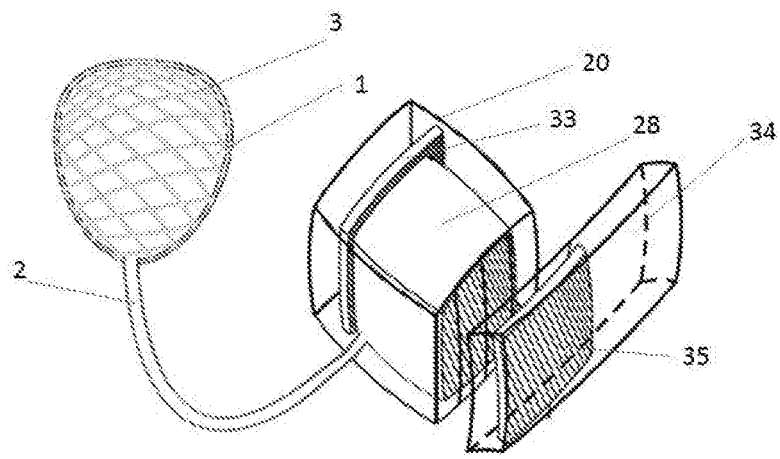
FIG. 13 is a schematic diagram of the double chamber extrusion driving system with a magnetic squeeze drive structure of sliding on and off magnetic field generators.

As shown in FIGS. 8 and 13, the power system of the invention is a double chamber extrusion driving system with a magnetic squeeze drive structure, including a first driving pad 19 capable of generating a magnetic field, a second driving pad 21 containing a magnetic material, a driving chamber 17 formed by elastic outer walls, a driving medium 23 as liquid or gas, a driving tube 16, a driving holder 20 and a power supply 18, where the first driving pad 19 is provided on the driving holder 20. The first driving pad 19 is fixedly connected to one side of the driving chamber 17 and further fixedly connected to one side of the driving holder 20. The second driving pad 21 is fixedly connected to the other side of the driving chamber 17 and is opposite to the first driving pad 19. The first driving pad 19 and the second driving pad 21 are divided by the driving chamber 17. The power supply 18 is connected to the first driving pad 19, and the driving chamber 17 is filled with the driving medium 23. The driving tube 16 is respectively connected to the driving chamber 17 and the balloon-like structure 1. When the power supply 18 is started, the first driving pad 19 generates a magnetic field to attract the second driving pad 21 to move toward the first driving pad 19, so that the driving medium 23 in the driving chamber 17 is extruded through the driving tube 16 to pressurize the balloon-like structure 1 to expand to be a contractile configuration. When the power supply 18 is turned off, the magnetic field generated by the first driving pad 19 disappears and the second driving pad 21 is disengaged from the first driving pad 19. Meanwhile, the driving chamber 17 is stretched by the elastic outer walls to expand and recover, so that the driving medium 23 is to stretch sucked to return to the driving chamber 17 through the driving tube 16, decompressing the balloon-like structure 1 from contractile to be a diastolic configuration.

Figure 9:
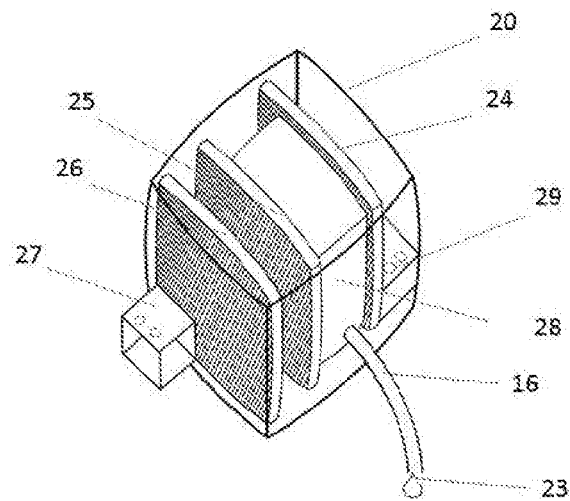
FIG. 9 is a schematic diagram of a magnetic squeeze drive structure of double magnetic generators.

As shown in FIGS. 9 and 13, the power system of the invention is a double chamber extrusion driving system with a magnetic squeeze drive structure, including a third driving pad 24 capable of generating a magnetic field, a fourth driving pad 25 containing a magnetic material, a fifth driving pad 26 capable of generating a magnetic field, a driving chamber 28 made of an inelastic material, a driving medium 23, a driving tube 16, a driving holder 20, a first power supply 29 and a second power supply 27, where the third driving pad 24 is fixedly connected to one side of the driving chamber 28 and further fixedly connected to one side of the driving holder 20. The fourth driving pad 25 is fixedly connected to the other side of the driving chamber 28 and is at the opposite to the third driving pad 24. The third driving pad 24 and the fourth driving pad 25 are divided by the driving chamber 28. The fifth driving pad 26 is fixedly connected to the other side of the driving holder 20, and is at the same side with the fourth driving pad 25 and adjacent to the fourth driving pad 25. The driving chamber 28 is filled with the driving medium 23, and the driving tube 16 is respectively connected to the driving chamber 28 and the balloon-like structure 1. The first power supply 29 and the second power supply 27 are respectively connected to the third driving pad 24 and the fifth driving pad 26. When the first power supply 29 is started, the third driving pad 24 generates a magnetic field to attract the fourth driving pad 25 to move toward the third driving pad 24, so that the driving medium 23 in the driving chamber 28 is extruded through the driving tube 16 to pressurize the balloon-like structure 1 to expand to be in a contractile configuration. When the first power supply 29 is turned off and the second power supply 27 is started, the magnetic field generated by the third driving pad 24 disappears and the fifth driving pad 26 generates a magnetic field, so that the fourth driving pad 25 is disengaged from the third driving pad 24 and the fifth driving pad 26 attracts the fourth driving pad 25 to move toward the fifth driving pad 26 to stretch the driving chamber 28 to recover. Meanwhile, the driving medium 23 is sucked to return to the driving chamber 28 through the driving tube 16, decompressing the balloon-like structure 1 from contractile to be a diastolic configuration.

Figure 10:
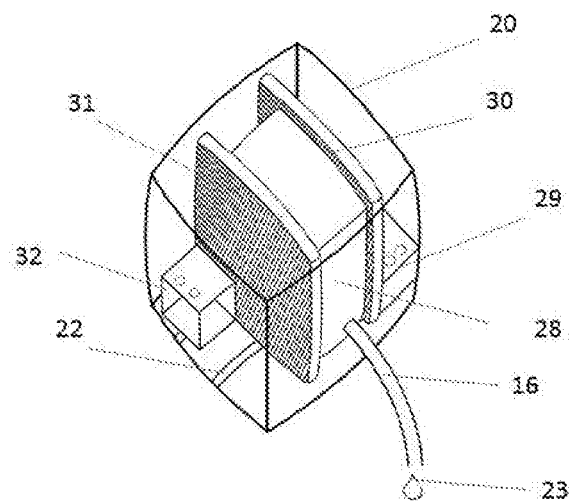
FIG. 10 is a schematic diagram of a magnetic squeeze drive structure of double polar magnetic field generators

As shown in FIGS. 10 and 13, the power system of the invention is a double chamber extrusion driving system with a magnetic squeeze drive structure, including a sixth driving pad 30 capable of generating a polar magnetic field, a seventh driving pad 31 capable of generating a polar magnetic field, a driving chamber 28 formed by inelastic outer walls, a driving medium 23, a driving tube 16, a driving holder 20, a first power supply 29 and a second power supply 32, where the sixth driving pad 30 is fixedly connected to one side of the driving chamber 28 and further fixedly connected to one side of the driving holder 20. The seventh driving pad 31 is fixedly connected to the other side of the driving chamber 28 and is at the opposite of the sixth driving pad 30. The sixth driving pad 30 and the seventh driving pad 31 are divided by the driving chamber 28. The first power supply 29 is connected to the sixth driving pad 30 and the second power supply 32 is connected to the seventh driving pad 31. The driving chamber 28 is filled with the driving medium 23, and the driving tube 16 is respectively connected to the driving chamber 28 and the balloon-like structure 1. When the first power supply 29 and the second power supply 32 are started at the same time, the sixth driving pad 30 and the seventh driving pad 31 both generate a magnetic field with the opposite polarity toward each other, so the seventh driving pad 31 is attracted to the sixth driving pad 30, the seventh driving pad 31 moves toward the sixth driving pad 30, and the driving chamber 28 is compressed and then it drives the driving medium 23 inside the driving chamber 28 into the balloon-like structure 1 through the driving tube 16 to pressurize the balloon-like structure 1 to expand to be a contractile configuration. When either the driving power supply 29 or the driving power supply 32 is switched in polarity of magnetic field to opposite direction, the seventh driving pad 31 is disengaged from the sixth driving pad 30 and is driven by repulsion to be away from the sixth driving pad 30, so that the driving chamber 28 is stretched to expand and recover. Meanwhile, the driving medium 23 is sucked to return to the driving chamber 28 through the driving tube 16, decompressing the balloon-like structure 1 be shrinked to be a diastolic configuration.

Figure 11:
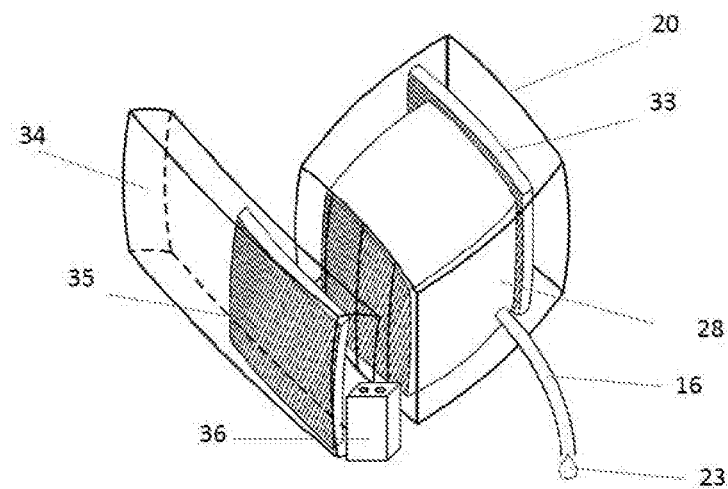
FIG. 11 is a schematic diagram of a magnetic squeeze drive structure of sliding on and off magnetic field generators.

As shown in FIGS. 11 and 13, the driving device of the invention has a push-pull movement structure. The internal driving pad 33 comprises a magnetic material and is provided inside the driving device. The external driving pad 35 comprises a permanent magnet and is provided outside the driving device. The internal driving pad 33 and the external driving pad 35 are divided by a driving chamber 28 provided there between. A sliding holder 34 is provided at the outside of the driving device for the left-to-right sliding of the driving pads. The external driving pad 35 is provided in the sliding holder 34, and can be pushed and pulled to move left and right by mechanical power device 36. When the external driving pad 35 moves to an action site corresponding to the internal driving pad 33, the internal driving pad 33 is attracted to move toward the external driving pad 35, and the driving chamber 28 is pressed to allow the driving medium 23 to flow into the balloon-like structure 1. Subsequently, the balloon-like structure 1 expands to be a contractile configuration. When the external driving pad 35 is moved away from the action site, the driving chamber 28 undergoes elastic recovery to push the internal driving pad 33 to move inward away from the external driving pad 35, so that the driving chamber 28 is stretched to allow the driving medium 23 to return to the driving chamber 28 through the driving tube 16, shrinking the balloon-like structure 1 to be a diastolic configuration.

Figure 12:
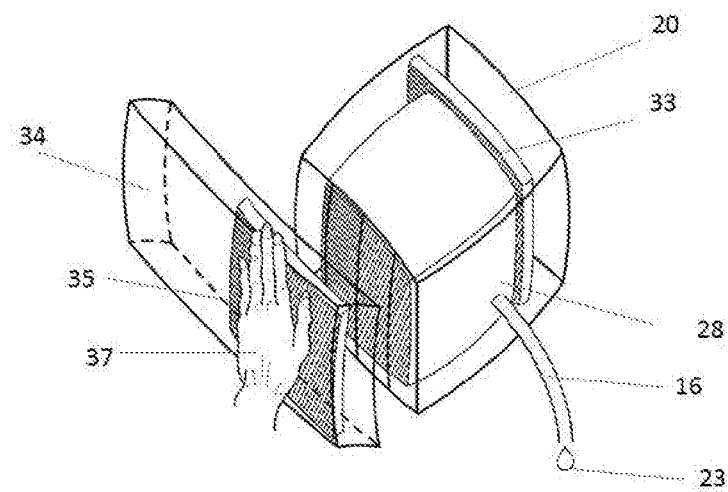
FIG. 12 is a schematic diagram of a magnetic squeeze drive structure of sliding on and off magnetic field generators by hand.

As shown in FIGS. 12 and 13, the driving device of the invention has a push-pull movement structure. The internal driving pad 33 comprises a permanent magnet and is provided inside the driving device. The external driving pad 35 comprises a permanent magnet and is provided outside the driving device. The internal driving pad 33 and the external driving pad 35 are divided by a driving chamber 28 provided there between. A sliding holder 34 is provided at the outside of the driving device for the left-to-right sliding of the driving pads. The external driving pad 35 is provided in the sliding holder 34, and can be pushed and pulled to move left and right by hand 37 in emergency. When the external driving pad 35 moves to an action site corresponding to the internal driving pad 33, the internal driving pad 33 is attracted to move toward the external driving pad 35, so that the driving chamber 28 is pressed to allow the driving medium 23 to flow into the balloon-like structure 1, and expands the balloon-like structure 1 to be a contractile configuration. When the external driving pad 35 is moved away from the action site, the driving chamber 28 undergoes elastic recovery to drive the internal driving pad 33 to move inward away from the external driving pad 35, so that the driving chamber 28 is stretched to allow the driving medium 23 to return to the driving chamber 28 through the driving tube 16, shrinking the balloon-like structure 1 to be a diastolic configuration.

Figure 14:
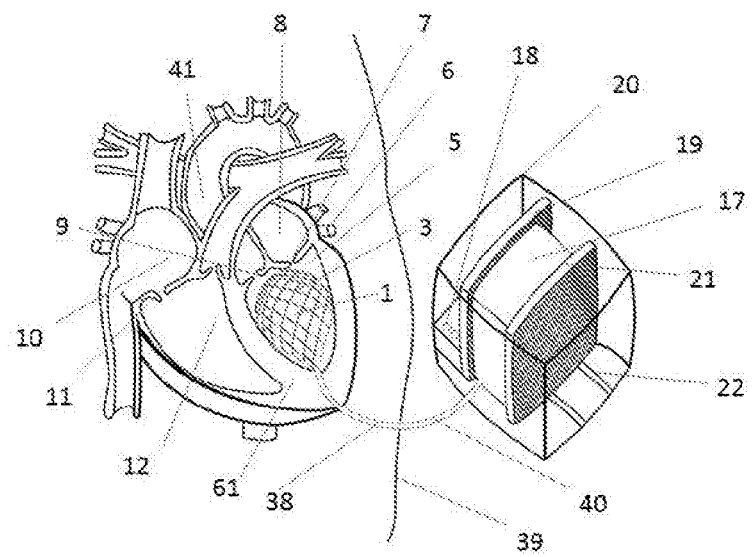
FIG. 14 is a schematic diagram of a communication setting of the ventricular assist device through a driving medium between outside the body and inside the body.

As shown in FIGS. 13 and 14, the structure of the invention for implantable ventricular assist device is a system in which the portion inside the body and the portion outside the body are communicated directly through a driving medium circulation, which includes an intraventricular stent 3, a balloon-like structure 1, a first driving pad 19, a second driving pad 21, a driving chamber 17, the driving medium, a power supply 18, an inner part of the driving tube 38 and an outer part of the driving tube 40, where the driving chamber 17 is filled with the driving medium as liquid or gas. The intraventricular stent 3, the balloon-like structure 1 and the inner part 38 are all provided inside the body, while the outer part of the driving tube 40, the power supply 18, the driving chamber 17 are all provided outside the body. The inner part 38 communicates with the outer part 40 through the driving tube cross the chest wall 39. The driving medium is circulated between the inner part 38 and the outer part 40 of the driving tube, and the balloon-like structure 1 and the driving chamber 17 to drive the balloon-like structure 1 to change between a contractile configuration and a diastolic configuration.

Figure 15:
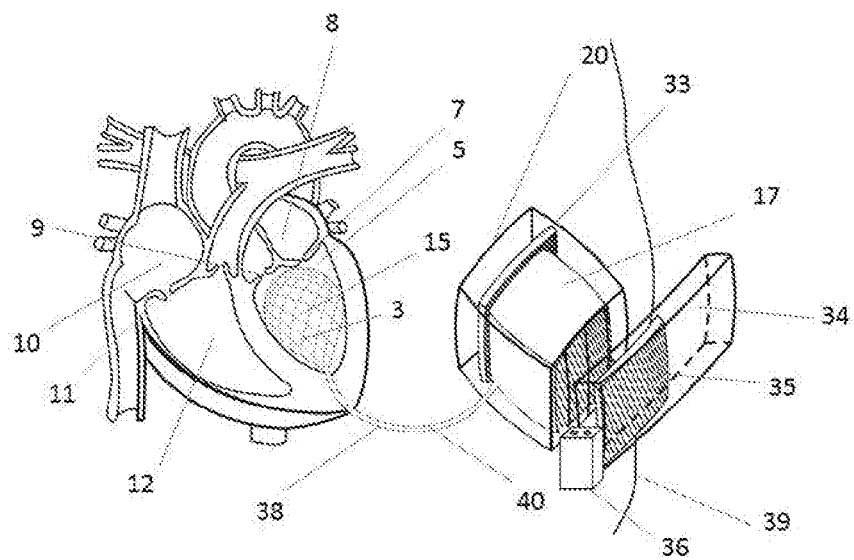
FIG. 15 is a schematic diagram of an separated setting of the ventricular assist device cross chest wall between outside the body and inside the body.
Figure 16:
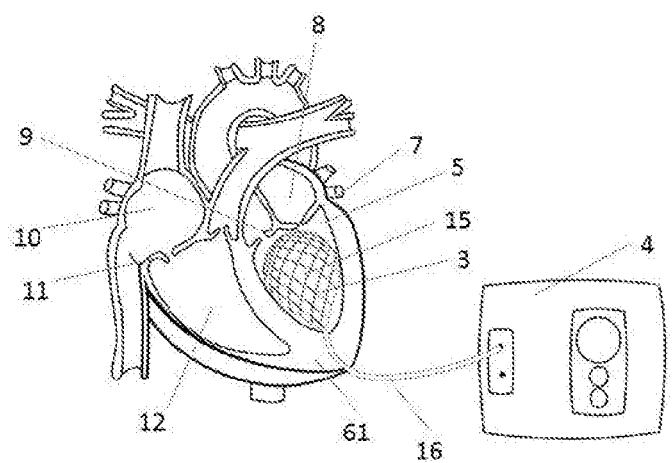
FIG. 16 is a schematic diagram of a one ventricle setting of the ventricular assist device implanted through the ventricular wall.
Figure 17:
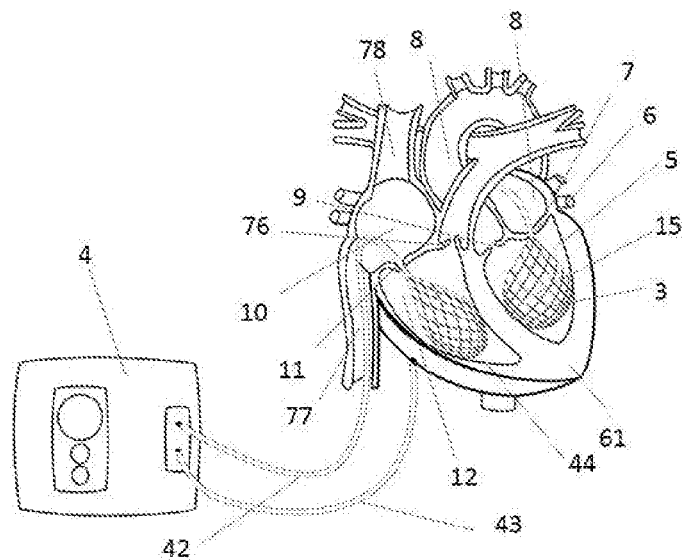
FIG. 17 is a schematic diagram of a two ventricles setting of the ventricular assist device implanted through the patient's vasculature.
Figure 18:
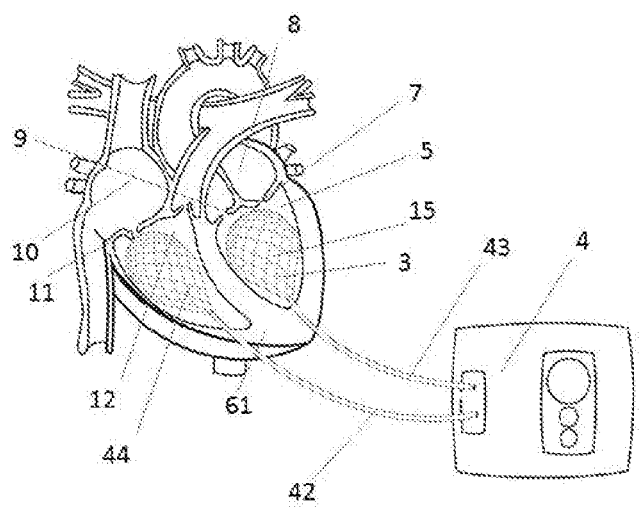
FIG. 18 is a schematic diagram of a two ventricles setting of the ventricular assist device implanted through the ventricular wall.

As shown in FIGS. 11, 13 and 15, the structure of the invention for implantable ventricular assist device is a separated system in which the portion inside the body and the portion outside the body have no direct contact and no direct driving medium mediated communication, which includes an intraventricular stent 1, a balloon-like structure 1, an internal driving pad 33, an external driving pad 35, a driving chamber 17, a power supply 36, the driving medium 23, an inner part 38 of the driving tube and an outer part 40 of the driving tube, where the driving chamber 17 is filled with the driving medium 23. The internal driving pad 33 comprises a magnetic material and the external driving pad 35 comprises a magnetic field generator. The driving chamber 28 with a resilient outer wall is filled with the driving medium 23. The intraventricular stent 3, the balloon-like structure 1, the internal driving pad 33, the driving chamber 17, the driving medium 23 and the driving tube 38, the driving tube 40 are all provided inside the body, where the internal driving pad 33 is fixedly connected to an inner side surface of the driving chamber 17. The external driving pad 35 is provided outside the body and is divided from the internal driving pad 33 by the chest wall 39 and free from the outer side wall of the driving chamber 17. When the external driving pad 35 at the outside generates a magnetic field, the internal driving pad 33 inside is attracted to move outward to the external driving pad 35 and compresses the driving chamber 17, so that the driving medium 23 is driven to flow into the balloon-like structure 1 through the driving tube 38 and the driving tube 40. Subsequently, the balloon-like structure 1 expands to be a contractile configuration. When the magnetic field generated by the external driving pad 35 disappears, the internal driving pad 33 is disengaged from the external driving pad 35 to make the driving chamber 17 elastically recover, so that the driving chamber 17 is stretched to allow the driving medium 23 in the balloon-like structure 1 to return to the driving chamber 17 through the driving tube 40 and the driving tube 38, shrinking the balloon-like structure 1 to be a diastolic configuration.

As shown in FIGS. 16-18, 26, the structure of the invention for implantable ventricular assist device can be arranged in a trans-ventricular wall or trans-blood vessel manner. For the trans-ventricular wall manner, a combination of an intraventricular stent 1 and a balloon-like structure 1 in the ventricle is connected to a power system 4 outside the ventricle through a driving tube 16 passing through the ventricular wall 61. And in the trans-blood vessel manner, a combination of the intraventricular stent 1 and the balloon-like structure 1 in the ventricle is connected to the power system 4 outside the ventricle through the driving tube passing through a heart valve into the blood vessel, which includes tricuspid valve 11, aortic valve 9, mitral valve 7, and pulmonary valve 76. This implantable device includes a single chamber setting and a double chamber setting. The implantation for the single chamber left ventricle setting can be performed by direct emplacement through trans-ventricular wall of open heart surgery, and also can be done via the patient's vasculature in a minimally-invasive procedure as artery 41, pulmonary vein 6 and left atrium 8. The implantation for the double chamber right ventricle setting can be performed by direct emplacement through trans-ventricular wall of open heart surgery, and also can be done via the patient's vasculature in a minimally-invasive procedure as femoral vein 77, subclavian vein 78 and right atrium 10.

Figure 19:
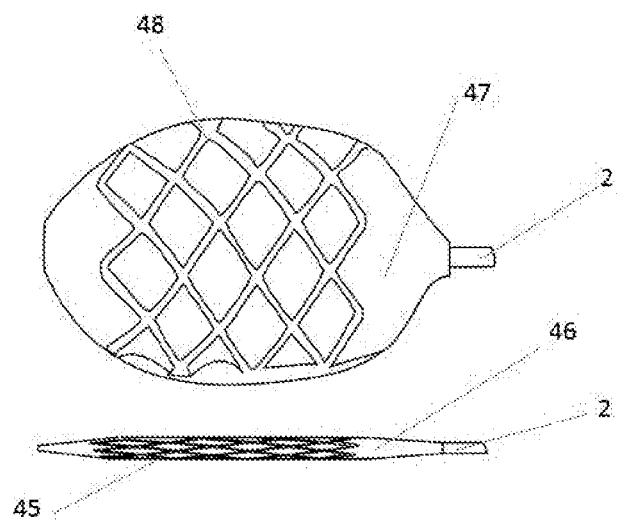
FIG. 19 is a schematic diagram of a comparison of external compression structure and internal extension structure.

As shown in FIG. 19, the structure of the invention for implantable ventricular assist device includes an implantable compacted package, where the implantable compacted package includes an compacted intraventricular stent 45 and a compacted balloon-like structure 46 and a driving tube 2. It can be delivered to the ventricle through a patient's blood vessel via minimally invasive procedure. After being implanted, the implantable compacted package can be extended and expanded to fit the longitudinal and lateral tensions of the inner surface of the ventricle, and establish an artificial chamber, where the implantable ventricular assist device includes an expanded intraventricular stent 48 and an expanded balloon-like structure 47 and a driving tube 2. The intraventricular stent 45 of the invention is made of a memory metal and forms a compacted package integrally with the balloon-like structure 46 before being placed in the heart, and after being placed in the heart, the intraventricular stent extends to form a three-dimensional mesh-like hollow supporting structure 48.

Figure 20:
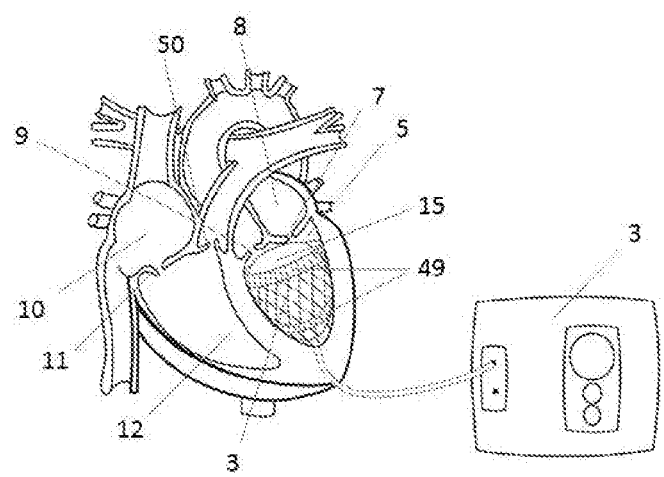
FIG. 20 is a schematic diagram of the fence-surround intraventriclular stent with anchor member.

As shown in FIG. 20, the intraventricular stent 3 of the invention includes a radially compressible and expandable anchoring member 49, where the anchoring member 49 can be provided at the inner surface at the upper portion of the ventricular wall 61 and at the inner surface directly below the atrioventricular valve 7 and 9, so the ventricle can be kept in an appropriate shape inside.

Figure 21:
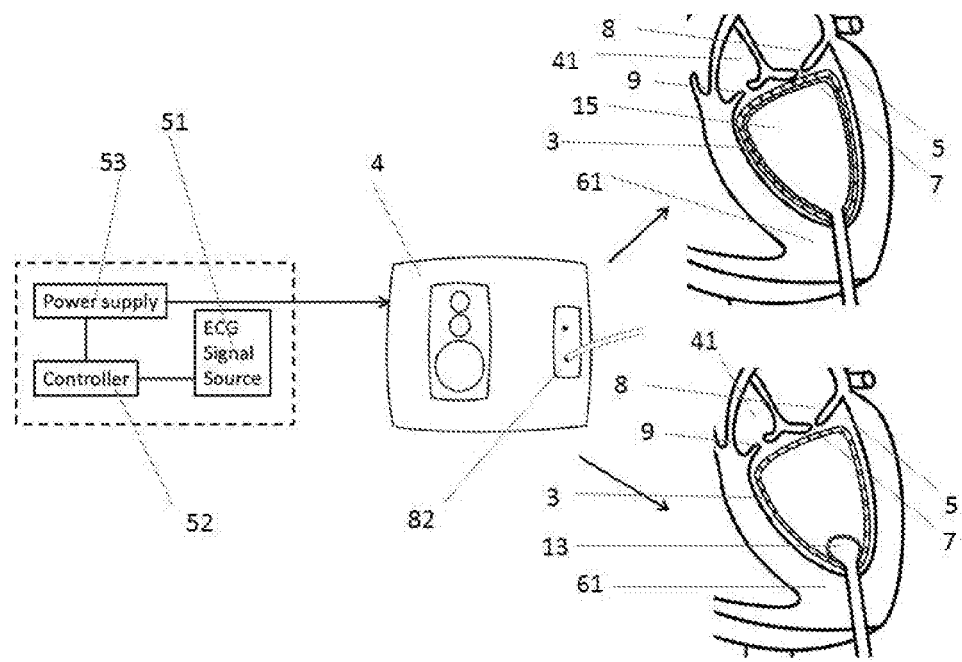
FIG. 21 is a schematic diagram of the activity of the balloon-like structure in cage-like intraventricular stent is controlled by ECG signal.
Figure 25:
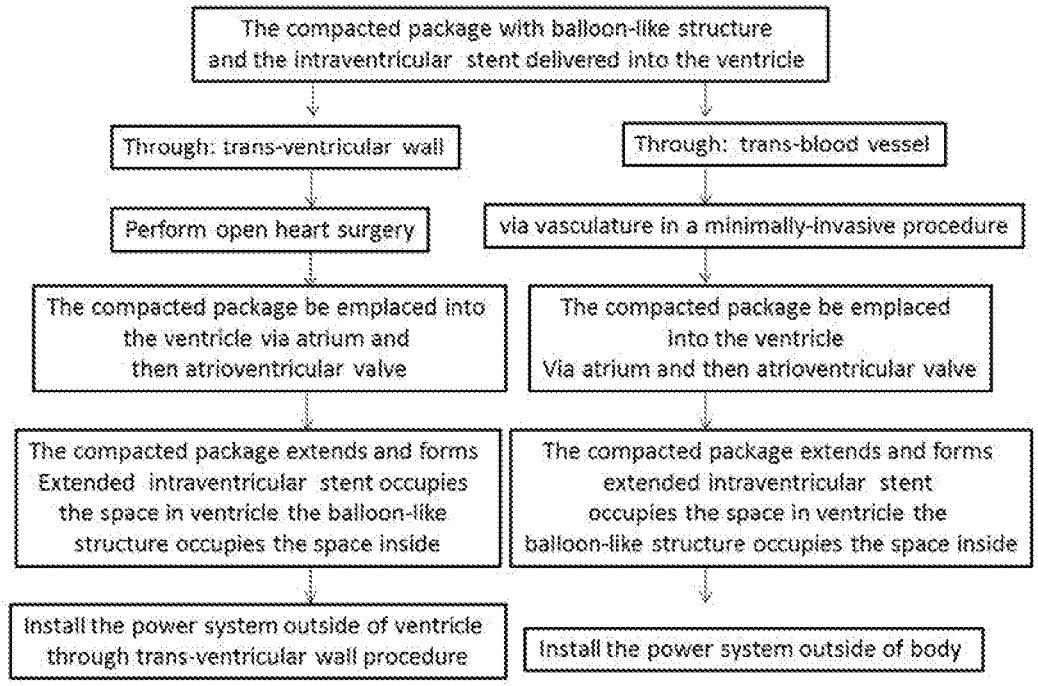
FIG. 25 is a schematic diagram of the action process of the balloon-like structure is controlled by ECG signal.
Figure 26:
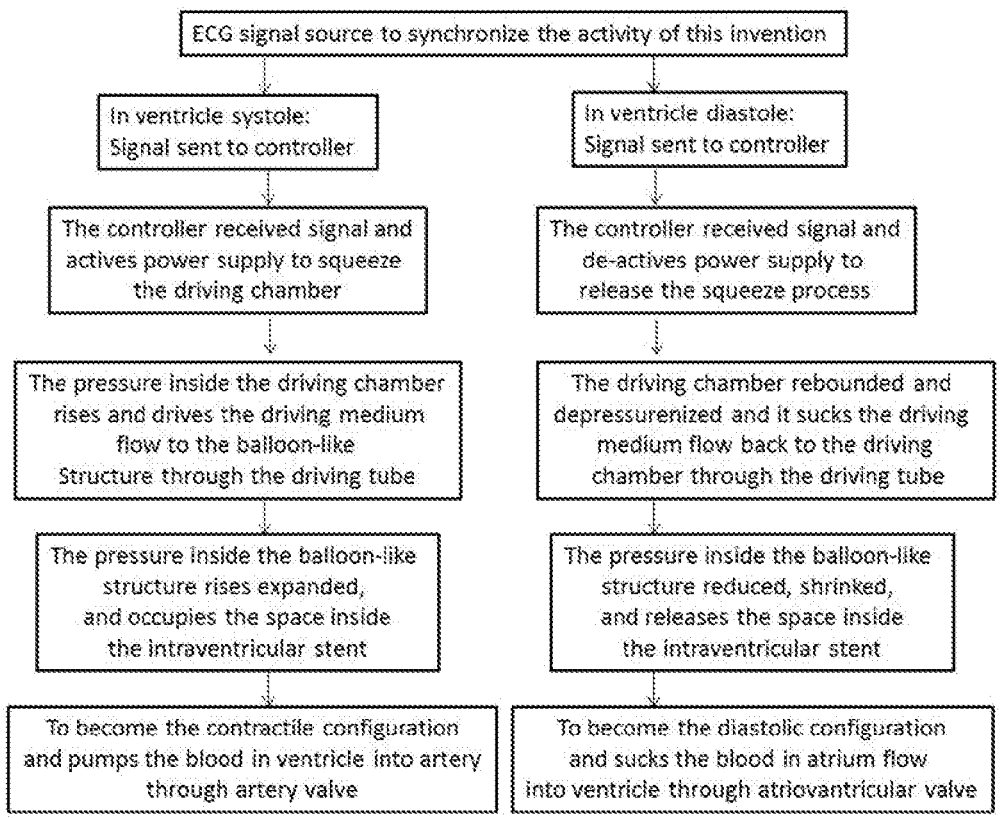
FIG. 26 is a schematic diagram of the implantation process of the balloon-like structure combined with the intraventricular stent to be delivered into the ventricle.

As shown in FIGS. 13 and 21, 25, the activity of the balloon-like structure 1 is controlled by ECG signal, the driving system includes an power supply 53 electrically connected to the magnetic field generator 82, a controller 52 which controls the power supply 53 to turn either on or off the magnetic field generation, and an ECG signal generator 51 which connect to the controller generates a signal when there is ventricular systole and ventricular diastole, wherein the artificial chamber is created by the cage-like intraventricular stent 3. When the ECG signal generator 51 signals the controller 52 that there is ventricular systole, the controller 52 controls the balloon-like structure 1 expanded, so that the blood is driven to flow into the artery 41 through the artery valve 9. When the ECG signal generator 51 signals the controller 52 that there is ventricular diastole, the controller 52 controls the balloon-like structure 1 decompressed to be a diastolic configuration. At this point, the blood in the atrium 8 is sucked to flow into the ventricle 5 through the atrioventricular valve 7.

Figure 22:
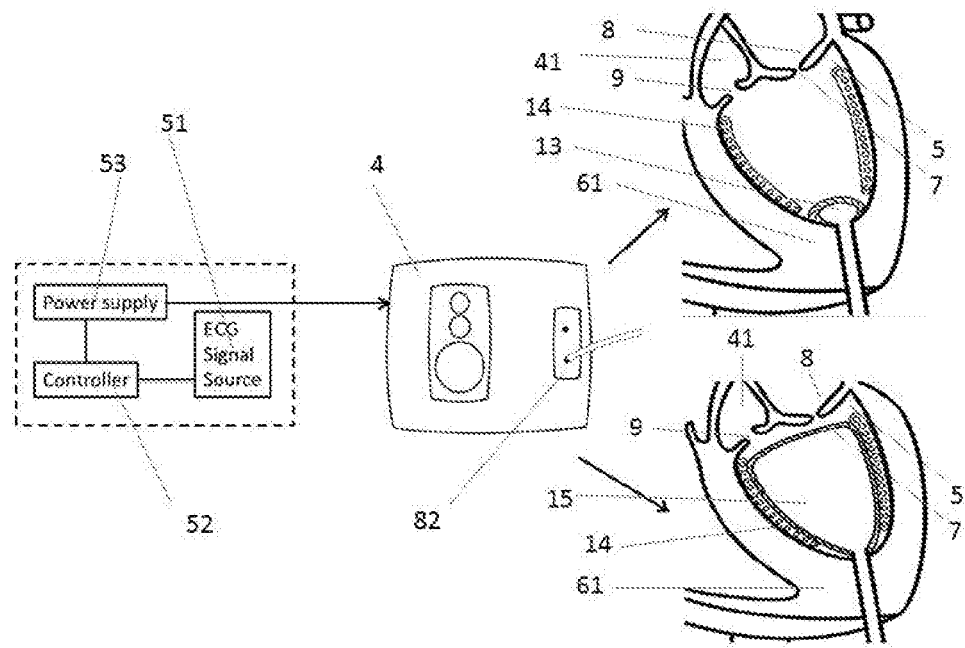
FIG. 22 is a schematic diagram of the activity of the balloon-like structure in fence-surround intraventricular stent with open top and bottom is controlled by ECG signal.

As shown in FIGS. 13 and 22, 25, the activity of the balloon-like structure 1 is controlled by ECG signal, the driving system includes an power supply 53 electrically connected to the magnetic field generator 82, a controller 52 which controls the power supply 53 to turn either on or off the magnetic field generation, and an ECG signal generator 51 which connect to the controller generates a signal when there is ventricular systole and ventricular diastole, wherein the artificial chamber is created by the fence-surround intraventricular stent with open end of top and bottom 14. When the ECG signal generator 51 signals the controller 52 that there is ventricular systole, the controller 52 controls the balloon-like structure 1 expanded, so that the blood is driven to flow into the artery 41 through the artery valve 9. When the ECG signal generator 51 signals the controller 52 that there is ventricular diastole, the controller 52 controls the balloon-like structure 1 decompressed to be a diastolic configuration. At this point, the blood in the atrium 8 is sucked to flow into the ventricle 5 through the atrioventricular valve 7.

Figure 23:
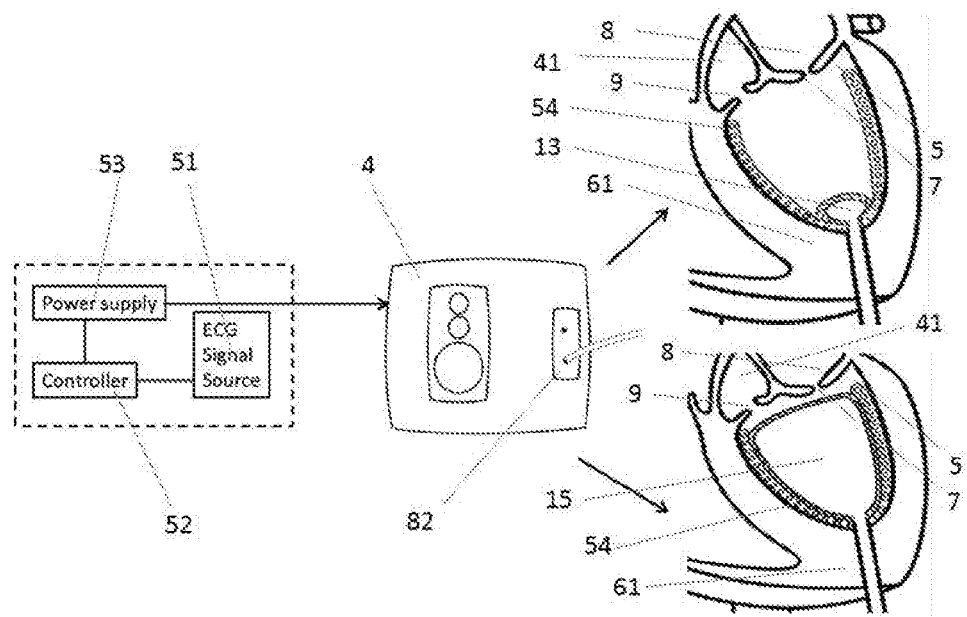
FIG. 23 is a schematic diagram of the activity of the balloon-like structure in fence-surround intraventricular stent with open top is controlled by ECG signal.

As shown in FIGS. 13 and 23, 25, the activity of the balloon-like structure 1 is controlled by ECG signal, the driving system includes an power supply 53 electrically connected to the magnetic field generator 82, a controller 52 which controls the power supply 53 to turn either on or off the magnetic field generation, and an ECG signal generator 51 which connect to the controller generates a signal when there is ventricular systole and ventricular diastole, wherein the artificial chamber is created by the fence-surround intraventricular stent with open end of top only 54. When the ECG signal generator 51 signals the controller 52 that there is ventricular systole, the controller 52 controls the balloon-like structure 1 expanded, so that the blood is driven to flow into the artery 41 through the artery valve 9. When the ECG signal generator 51 signals the controller 52 that there is ventricular diastole, the controller 52 controls the balloon-like structure 1 decompressed to be a diastolic configuration. At this point, the blood in the atrium 8 is sucked to flow into the ventricle 5 through the atrioventricular valve 7.

Figure 24:
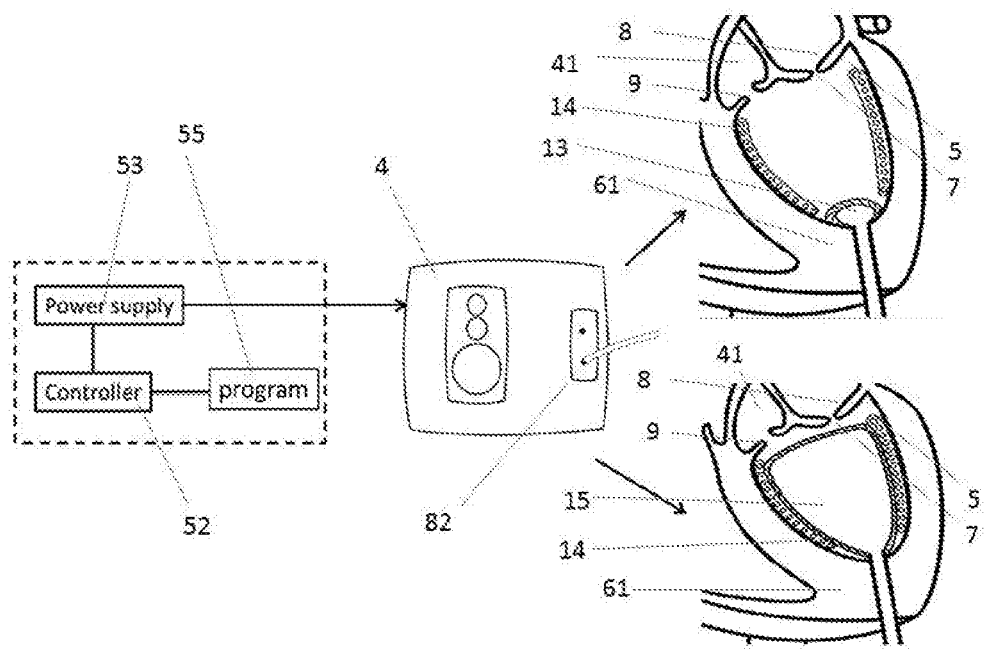
FIG. 24 is a schematic diagram of the activity of the balloon-like structure in fence-surround intraventricular stent with open top and bottom is controlled by programed controller.

As shown in FIGS. 13 and 24, the activity of the balloon-like structure 1 is controlled by a self-driven program controller 52, the driving system includes an power supply 53 electrically connected to the magnetic field generator 82, a controller 52 which controls the power supply 53 to turn either on or off the magnetic field generation and controls the change of contractile configuration and diastolic configuration; and an driving program 55 including a contractile rhythm, diastolic rhythm, contractile duration and diastolic duration is set up in the controller 52; wherein the controller 52 controls the balloon-like structure 1 expanded when the controller 52 generates a signal that there is contractile rhythm and the controller 52 controls the balloon-like structure 1 to shrink when the controller 52 generates a signal that there is diastolic rhythm. When a systole driving is started to pressurize the balloon-like structure 1 to expand to be a contractile configuration, the blood is driven to flow into the artery through the artery valve. When a diastole driving is started to decompress the balloon-like structure 1 shrinked to be a diastolic configuration, the blood in the atrium 8 is sucked to flow into the ventricle 5 through the atrioventricular valve 7.

The performance of the invention will be further illustrated with reference to specific experiments.

Figure 27:
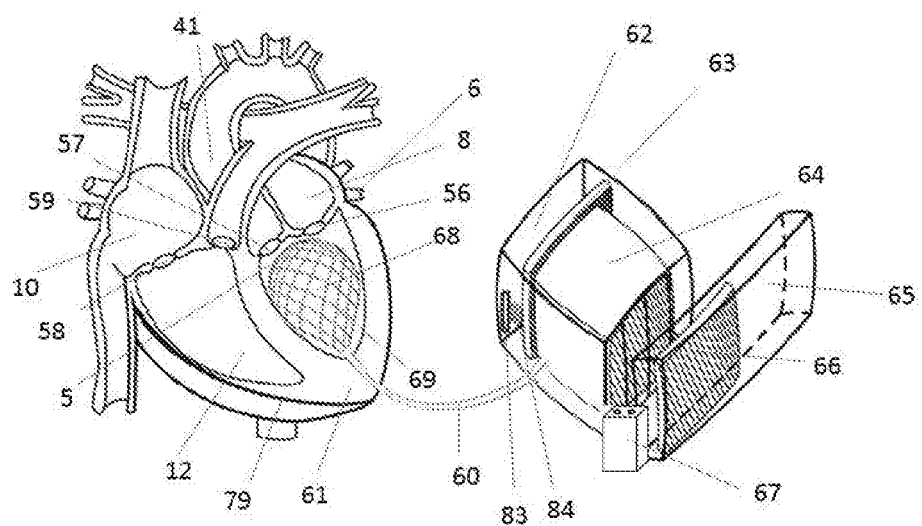
FIG. 27 is a schematic diagram of the experimental structure of the ventricular assist device in example 1.

Example 1 Observation on the Ventricular Assisting Effect of a Closed Intraventricular Stent (Referring to FIG. 27, 29)

The experimental materials included a heart model, a stainless steel wire, a stainless steel rod, a latex balloon, a silicon tube, a waterproof polyester fiber chamber, a permanent magnet pad, a servo motor, a battery and a spring.

The experimental device was prepared as follows. The heart model 79 with a ventricle volume of about 100 mL was established by 3D printing, which includes the front half and the rear half printed separately and then sealed together for a whole heart. Each valve of the heart model was replaced with a check valve, which was, the check valve was fixedly bound to the site where the heart valve should be. A cage-like intraventricular stent 69 was prepared from the stainless steel wire. A latex balloon 68 with a volume of about 100 mL was prepared with 1 mm-thick latex. The driving chamber 64 having a volume of about 120 mL was prepared from the waterproof polyester fiber and was close bound to the silicon tube 60 at the outlet end. A first permanent magnet pad 63 was fixedly bound to one side of the driving chamber 64. A driving device holder 62 was prepared and a sliding rail 75 was disposed at the bottom. A slide holding bracket 83 was provided on the first permanent magnet pad 63. A dragging spring 84 was fixedly disposed between a rear end of the slide holding bracket 83 and the driving device holder 62. The driving chamber 64 was placed on the driving device holder 62, and was fixedly attached to the side of the slide holding bracket 83 where the first permanent magnet pad 63 was bound. A driving displacement bracket 65 was prepared for the placement of a second permanent magnet pad 66, which allowed the second permanent magnet pad 66 to move to the left and right on the bracket 65. A supporting pad capable of sliding left and right was provided on the driving displacement bracket 65, where the second permanent magnet pad 66 was provided at an inner side of the supporting pad and an outer side of the supporting pad was provided with the servo motor 67 which was connected with the battery to drive the supporting pad to move left and right. The driving displacement bracket 65 was fixedly connected to the driving device holder 62 and to ensure that when the supporting pad moved to the right side, the second permanent magnet pad 66 was corresponded to the first permanent magnet pad cross the driving chamber 64. The driving chamber 64 was filled with deionized water, and then the air in the latex balloon 68 was emptied. The other end of the silicone tube 60 was closely bound to an interface end of the latex balloon 68, and the latex balloon 68 was placed inside the cage-like intraventricular stent 69. The front half and rear half of the heart model were opened to expose the driving chamber 64, and then the cage-like intraventricular stent 69 and the latex balloon 68 were sequentially emplaced in the ventricle 5 and had the driving tube 60 connected with the latex balloon 68 to pass through the ventricular wall 61. The front half and rear half of the heart model were closed and formed the experimental model of the invention.

The experimental method and results were described as follows. Connected the liquid inlet with the pulmonary vein 6, and further connected to a deionized water output, so that the deionized water filled into the atrium 8 and the ventricle 5. The second permanent magnet pad 66 was manually moved to the right side, it attracted the first permanent magnet pad 63 and we saw the first permanent magnet pad 63 simultaneously moves along the sliding rail 75 toward the second permanent magnet pad 66 to pressurize the driving chamber 64, the water in the driving chamber 64 was driven to flow into the latex balloon 68 through the driving tube 60 to expand the latex balloon 68, and then the water in the cage-like intraventricular stent 69 was driven out and then pushed the water in the ventricle 5 to enter the aorta 41 through the artery valve 57 and then discharged. Furthermore, when the second permanent magnet pad 66 was manually moved to the left side, the attraction between two pads was disappeared and the first permanent magnet pad 63 was dragged back by the dragging spring 84 to move away from the second permanent magnet pad 66 along the sliding rail 75 and the driving chamber 64 was stretched expansion to recover, the liquid in the latex balloon 68 was sucked to flow back into the driving chamber 64 through the driving tube 60 and had the latex balloon 68 shrinked, and then the deionized water in the left atrium 8 was sucked to enter the left ventricle 5 through the mitral valve 56. After that we started the servo motor 67 with a speed set at 60 rpm, and at this point, the deionized water was observed to be intermittently ejected from the outlet of the aorta 41 at a frequency of 60 times/min. These results show that the system of the invention operates normally and successfully.

Figure 28:
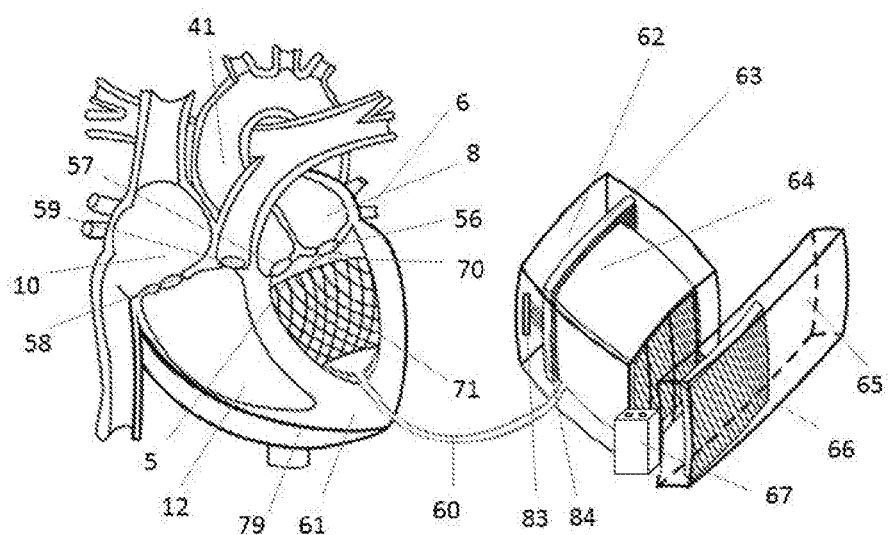
FIG. 28 is a schematic diagram of the experimental structure of the ventricular assist device in example 2.
Figure 29:
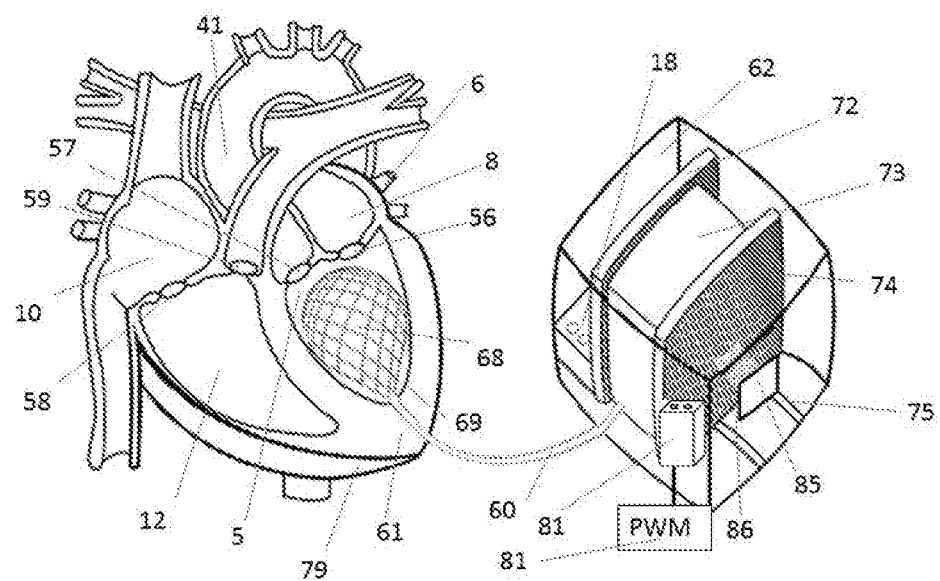
FIG. 29 is a schematic diagram of the experimental structure of the ventricular assist device in example 3.

Example 2 Observation on the Ventricular Assisting Effect of an Open Intraventricular Stent (Referring to FIGS. 28, 29)

The experimental materials were referred to Example 1.

The preparation of the experimental device in this example was basically identical with Example 1 except for the use of a round-tubular upper-lower opened intraventricular stent.

The experimental method and results were described as follows. Connected the liquid inlet with the pulmonary vein 6, and further connected to a deionized water output, so that the deionized water filled into the atrium 8 and the ventricle 5. The second permanent magnet pad 66 was manually moved to the right side, it attracted the first permanent magnet pad 63 and we saw the first permanent magnet pad 63 simultaneously moves along the sliding rail 75 toward the second permanent magnet pad 66 to pressurize the driving chamber 64, the water in the driving chamber 64 was driven to flow into the latex balloon 68 through the driving tube 60 to expand the latex balloon 70, and then the water in the round-tubular upper-lower opened intraventricular stent 71 (fence-surround intraventricular stent) was driven out and then pushed the water in the ventricle 5 to enter the aorta 41 through the artery valve 57 and then discharged. Furthermore, when the second permanent magnet pad 66 was manually moved to the left side, the attraction between two pads was disappeared and the first permanent magnet pad 63 was dragged back by the dragging spring 84 to move away from the second permanent magnet pad 66 along the sliding rail 75 and the driving chamber 64 was stretched expansion to recover, the liquid in the latex balloon 68 was sucked to flow back into the driving chamber 64 through the driving tube 60 and had the latex balloon 68 shrinked, and then the deionized water in the left atrium 8 was sucked to enter the left ventricle 5 through the mitral valve 56. After that we started the servo motor 67 with a speed set at 60 rpm, and at this point, the deionized water was observed to be intermittently ejected from the outlet of the aorta 41 at a frequency of 60 times/min. These results show that the system of the invention operates normally and successfully.

Example 3 Observation on the Ventricular Assisting Effect by Electromagnetic Driving System (Referring to FIG. 29)

The experimental materials included a PWM modulator, and an iron pad instead of the first permanent magnet pad and an electromagnetic pad instead of the second permanent magnet pad. The servo motor was not required here and other materials were referred to Example 1.

The experimental device was prepared as follows. The heart model 79 with a ventricle volume of about 100 mL was established by 3D printing, which includes the front half and the rear half printed separately and then sealed together for a whole heart. Each valve of the heart model was replaced with a check valve, which was, the check valve was fixedly bound to the site where the heart valve should be. A cage-like intraventricular stent 69 was prepared from the stainless steel wire. A latex balloon 68 with a volume of about 100 mL was prepared with 1 mm-thick latex. The driving chamber 73 having a volume of about 120 mL was prepared from the waterproof polyester fiber and was close bound to the silicon tube 60 at the outlet end. The iron pad 74 was fixedly bound to one side of the driving chamber 73. A driving device holder 62 was prepared and a sliding rail 75 was disposed at the bottom. A slide holding bracket 85 was provided on the sliding driving device holder 62. A dragging spring 86 was fixedly disposed between a front end of the iron pad 74 and the driving device holder 62. The driving chamber 73 was placed on the driving device holder 62, and was fixedly attached to the side of the driving device holder 62 where the electromagnetic pad 72 was bound. The PWM modulator 80 was provided on the outer side of the electromagnetic pad 72 and was connected to a battery 81 to adjust the frequency at which the battery 81 supplied power to the electromagnetic pad 72. The position of the electromagnet pad 72 at the outside was adjusted to correspond to the iron pad 74 located at the outer side cross the driving chamber 73. The driving chamber 73 was filled with deionized water, and then the air in the latex balloon 68 was emptied. The other end of the silicone tube 60 was closely bound to an interface end of the latex balloon 68, and the latex balloon 68 was placed inside the cage-like intraventricular stent 69. The front half and rear half of the heart model were opened to expose the driving chamber 73, and then the cage-like intraventricular stent 69 and the latex balloon 68 were sequentially emplaced in the ventricle 5 and had the driving tube 60 connected with the latex balloon 68 to pass through the ventricular wall 61. The front half and rear half of the heart model were closed and formed the experimental model of the invention.

The experimental method and results were described as follows. Connected the liquid inlet with the pulmonary vein 6, and further connected to a deionized water output, so that the deionized water filled into the atrium 8 and the ventricle 5. When the power supply 81 was turned on, we saw the iron pad 74 simultaneously moved along the sliding rail 75 toward the electromagnet pad 72 to pressurize the driving chamber 73, the water in the driving chamber 73 was driven to flow into the latex balloon 68 through the driving tube 60 to expand the latex balloon 68, and then the water in the cage-like intraventricular stent 69 was driven out and then pushed the water in the ventricle 5 to enter the aorta 41 through the artery valve 57 and then discharged. Furthermore, when the power was turned off, the iron pad 74 was dragged back by the dragging spring 86 to move away from the electromagnetic pad 72 along the sliding rail 75 and the driving chamber 73 was stretched expansion to recover, the water in the latex balloon 68 was sucked to flow back into the driving chamber 73 through the driving tube 60 and had the latex balloon 68 shrinked, and then the deionized water in the left atrium 8 was sucked to enter the left ventricle 5 through the mitral valve 56. After that we turned to the servo motor 67. The running speed from PWM modulator 80 was adjusted to be 60 rpm and the power was turned on, and at this point, the deionized water was observed to be intermittently ejected from the outlet of the aorta at a frequency of 60 times/min. These results show that the system of the invention operates normally and successfully.

These embodiments are merely illustrative of the invention, and various changes can be made to the invention with respect to the structure and connection of the components. Equivalent changes and modifications made based on the content of the invention should fall within the scope of the invention.

What is claimed is:

1. An implantable ventricular assist device comprising:
   an intraventricular stent used for the creation of an artificial chamber inside a ventricle by a three-dimensional mesh-like hollow supporting structure;
   a balloon-like structure is disposed inside the intraventricular stent to drive the change of the artificial chamber between a contractile configuration and a diastolic configuration, wherein in the contractile configuration, the balloon-like structure expands and occupies the space of the artificial chamber and drives the blood inside the artificial chamber to flow to outside the artificial chamber through the mesh-like structure of the intraventricular stent; wherein in the diastolic configuration, the balloon-like structure shrinks and releases the space inside the artificial chamber, and the blood outside the artificial chamber flows back into the artificial chamber through the mesh-like structure of the intraventricular stent;
   a power system for driving the change of the balloon-like structure between the contractile configuration and the diastolic configuration;
   wherein the power system comprises a magnetic squeeze drive structure which is used for driving the changes of the balloon-like structure between the contractile configuration and diastolic configuration, and comprises a driving pad, a driving chamber, a driving medium, a driving tube and a driving holder;—
   the driving chamber provided on the driving holder is a soft structure with a resilient outer wall and adjacent to a first driving pad and a second driving pad; the first driving pad is attached on the one side of the resilient outer wall of the driving chamber and further fixed on the one side of the driving holder, and the second driving pad is attached on the opposite side of the resilient outer wall of the driving chamber and free from the driving holder, the driving chamber is filled with the driving medium, and the first driving pad has a magnetic field generator and the second driving pad has a magnetic material which is able to be attracted to the magnetic field generator when the magnetic field generator generates a magnetic field; the driving chamber is compressible when the first driving pad generates a magnetic field and the second driving pad is attracted to the first driving pad and moves toward the first driving pad, so as to drive the driving medium inside the driving chamber into the balloon-like structure through the driving tube and expand the balloon-like structure to the contractile configuration; the driving chamber is able to be decompressed and restored by actuating the resilient outer wall of the driving chamber along with the second driving pad when the first driving pad stops generating a magnetic field and the second driving pad is not attracted to the first driving pad and released from the first driving pad, so as to suck the driving medium in the balloon-like structure to flow back into the driving chamber and shrink the balloon-like structure to the diastolic configuration.
2. The device of claim 1, the implantable ventricular assist device includes a cage-like intraventricular stent, the balloon-like structure, the driving tube and the power system, wherein:

the cage-like intraventricular stent is a closed three-dimensional hollow mesh-like structure, and forms a closed cage-like artificial chamber by itself;

the balloon-like structure disposed inside the cage-like intraventricular stent comprises a connector and a retractable three-dimensional balloon-like structure, and the connector is connected with the driving tube;

the driving tube is used for the connection between the power system and the balloon-like structure; wherein in the contractile configuration, the power system raises the pressure in the balloon-like structure, so the balloon-like structure expands, and the blood inside the artificial chamber is driven outside the artificial chamber into the ventricle, and then the blood in the ventricle is driven to flow into the artery through an artery valve; wherein in the diastolic configuration the power system decompresses the balloon-like structure, shrinks the balloon-like structure, releases the space inside the artificial chamber, and sucks the blood in the ventricle flow into the artificial chamber, and then sucks the blood from the atrium flow into the ventricle through an atrioventricular valve.

3. The device of claim 1, the implantable ventricular assist device includes a fence-surround intraventricular stent, the balloon-like structure, the driving tube and the power system, wherein:

the fence-surround intraventricular stent is a three-dimensional hollow mesh-like structure with an open end, and forms a closed artificial chamber by a fence-surrounded and a ventricular wall combined;

the balloon-like structure is disposed inside the fence-surround intraventricular stent comprising a connector and a retractable three-dimensional balloon-like structure, and the connector is connected with the driving tube;

the driving tube is used for the connection between the power system and the balloon-like structure; wherein in the contractile configuration, the power system raises the pressure in the balloon-like structure, so the balloon-like structure expands, and the blood inside the artificial chamber is driven outside the artificial chamber into the ventricle, and then the blood in the ventricle is driven to flow into the artery through an artery valve; wherein in the diastolic configuration, the power system decompresses the balloon-like structure, shrinks the balloon-like structure, releases the space inside the artificial chamber, and the blood in the ventricle flows back into the artificial chamber, and then the blood is sucked from the atrium and flow into the ventricle through an atrioventricular valve.

4. The device of claim 1, wherein the power system comprises a double chamber extrusion driving system, which is mediated by the driving medium comprising at least one of the mediums of liquid and gas.

5. The device of claim 1, wherein the magnetic field generator is an electromagnet; and the polarity of the electromagnet is controlled by changing the polarity of the electric power supply; or the magnetic field generator is a permanent magnet; and an action site of the magnetic field of the permanent magnet is controlled by the translocation of the permanent magnet.

6. The device of claim 1, wherein the activity of the balloon-like structure is controlled by an electrocardiography (ECG) signal, the driving system includes an electrical energy supply electrically connected to the magnetic field generator, a controller which controls the electric energy supply to turn either on or off the magnetic field generation, and an ECG signal generator which connects to the controller generates the ECG signal when there is ventricular systole and ventricular diastole, wherein the controller controls the balloon-like structure to expand when the ECG signal generator signals the controller that there is ventricular systole and wherein the controller controls the balloon-like structure to shrink when the ECG signal generator signals the controller that there is ventricular diastole.

7. The device of claim 1, wherein the driving system includes an electrical energy supply electrically connected to the magnetic field generator, a controller which controls the electric energy supply to turn either on or off the magnetic field generation and controls the change of contractile configuration and diastolic configuration; and a driving program including a contractile rhythm, diastolic rhythm, contractile duration and diastolic duration is set up in the controller; wherein the controller controls the balloon-like structure to expand when the controller generates a signal that there is contractile rhythm and wherein the controller controls the balloon-like structure to shrink when the controller generates a signal that there is diastolic rhythm.

8. The device of claim 1, wherein the intraventricular stent includes a radially compressible and expandable anchor member which is deployed inside an inner surface of a ventricular wall and the inner surface below an atrioventricular valve and the radially compressible and expandable anchor member is configured to keep the ventricle in shape.

9. The device of claim 1, wherein the implantable ventricular assist device is in a communication setting through a driving medium between outside the body and inside the body, which comprises the intraventricular stent, the balloon-like structure, the driving pad, the driving chamber, a power supply, the driving medium and the driving tube; the driving chamber is filled with the driving medium, wherein the portion inside the body includes the intraventricular stent, the balloon-like structure, and the internal part of the driving tube, wherein the portion outside the body includes the driving pad, the power supply and the driving chamber and the external part of the driving tube, and further the inside and outside portions of the implantable ventricular assist device are communicated by the driving tube across the chest wall, the driving medium is able to circulate between the inside and outside portions of the implantable ventricular assist device and drive the change of the balloon-like structure between the contractile configuration and diastolic configuration.

10. The device of claim 1, wherein the material for making the intraventricular stent is a flexible supporting material with elasticity, memory metal and anti-thrombosis characteristics.

11. The device of claim 1, wherein the material for making the balloon-like structure is a soft material with endurance, elasticity and anti-thrombosis characteristics.

12. The device of claim 1, wherein the intraventricular stent is an external compression structure and made by memory metal or other flexible stent materials and is integrated and compacted with the balloon-like structure before implantation, and after being implanted in the ventricle, the intraventricular stent is able to extend and form a three-dimensional hollow mesh-like supporting structure and apply a longitudinal and horizontal force against the inner surface of the ventricle to establish the artificial chamber.

13. The device of claim 1, wherein the implantable ventricular assist device comprises an implantable compacted package that is able to be delivered to the ventricle via the patient's vasculature in a minimally-invasive procedure and when the implantable compacted package is deployed inside the ventricle, the implantable compacted package is extended and adapted to apply a longitudinal force and horizontal force against the inner surface of the ventricle to establish the artificial chamber.

14. The device of claim 1, wherein an action site of the magnetic field is adjustable by the translocation of the magnetic field generator on the driving holder.

* * * * *